United States Patent
Racenet et al.

(10) Patent No.: US 10,092,294 B2
(45) Date of Patent: *Oct. 9, 2018

(54) SURGICAL INSTRUMENT WITH ELONGATED CHANNEL

(71) Applicant: Covidien LP, Mansfield, MA (US)

(72) Inventors: Danyel Racenet, Killingworth, CT (US); Thomas Wenchell, Durham, CT (US); Keith L. Milliman, Bethel, CT (US)

(73) Assignee: Covidien LP, Mansfield, MA (US)

( * ) Notice: Subject to any disclaimer, the term of this patent is extended or adjusted under 35 U.S.C. 154(b) by 61 days.

This patent is subject to a terminal disclaimer.

(21) Appl. No.: 15/289,269

(22) Filed: Oct. 10, 2016

(65) Prior Publication Data

US 2017/0020528 A1   Jan. 26, 2017

Related U.S. Application Data

(60) Continuation of application No. 14/183,573, filed on Feb. 19, 2014, now Pat. No. 9,463,023, which is a
(Continued)

(51) Int. Cl.
| | |
|---|---|
| *A61B 17/10* | (2006.01) |
| *A61B 17/115* | (2006.01) |
| *A61B 1/06* | (2006.01) |
| *A61B 1/313* | (2006.01) |
| *A61B 90/30* | (2016.01) |
| *A61B 17/072* | (2006.01) |
| *A61B 1/018* | (2006.01) |

(Continued)

(52) U.S. Cl.
CPC ............ *A61B 17/1155* (2013.01); *A61B 1/06* (2013.01); *A61B 1/3132* (2013.01); *A61B 17/00234* (2013.01); *A61B 17/072* (2013.01); *A61B 17/07207* (2013.01); *A61B 17/115* (2013.01); *A61B 90/30* (2016.02); *A61B 1/018* (2013.01); *A61B 2017/0034* (2013.01); *A61B 2017/07221* (2013.01); *A61B 2017/07257* (2013.01); *A61B 2017/07271* (2013.01); *A61B 2017/22072* (2013.01)

(58) Field of Classification Search
CPC ... A61B 17/068; A61B 17/105; A61B 17/115; A61B 17/114; A61B 17/10; A61B 17/00; A61B 17/22; A61B 17/072; A61B 17/1155; A61B 17/1114
See application file for complete search history.

(56) References Cited

U.S. PATENT DOCUMENTS

| | | |
|---|---|---|
| 4,473,077 A | 9/1984 | Noiles et al. |
| 4,576,167 A | 3/1986 | Noiles |
| (Continued) | | |

*Primary Examiner* — Victor Nguyen

(57) ABSTRACT

A surgical instrument including a handle assembly, an elongated body portion, a head portion and an elongated channel. The elongated body portion extends distally from the handle assembly. The head portion is disposed adjacent a distal end of the elongated body portion and includes an anvil assembly and a shell assembly. The elongated channel includes a proximal opening and a distal opening. The proximal opening is disposed distally of a proximalmost end of the handle assembly and proximally of the shell assembly. The distal opening is disposed on the shell assembly.

15 Claims, 7 Drawing Sheets

Related U.S. Application Data division of application No. 12/486,826, filed on Jun. 18, 2009, now Pat. No. 8,678,264.

(60) Provisional application No. 61/078,460, filed on Jul. 7, 2008.

(51) Int. Cl.
*A61B 17/00* (2006.01)
*A61B 17/22* (2006.01)

(56) References Cited

U.S. PATENT DOCUMENTS

| | | |
|---|---|---|
| 4,646,745 A | 3/1987 | Noiles |
| 5,005,749 A | 4/1991 | Aranyi |
| 5,119,983 A | 6/1992 | Green et al. |
| 5,403,326 A | 4/1995 | Harrison et al. |
| 5,483,951 A | 1/1996 | Frassica et al. |
| 5,588,579 A | 12/1996 | Schnut et al. |
| 5,868,760 A | 2/1999 | McGuckin, Jr. |
| 6,053,390 A | 4/2000 | Green et al. |
| 6,083,241 A | 7/2000 | Longo et al. |
| 6,102,271 A | 8/2000 | Longo et al. |
| 6,119,913 A | 9/2000 | Adams et al. |
| 6,126,058 A | 10/2000 | Adams et al. |
| 6,142,933 A | 11/2000 | Longo et al. |
| 6,179,195 B1 | 1/2001 | Adams et al. |
| 6,241,140 B1 | 6/2001 | Adams et al. |
| 6,264,086 B1 | 7/2001 | McGuckin, Jr. |
| 6,302,311 B1 * | 10/2001 | Adams ............... A61B 17/115 227/176.1 |
| 6,343,731 B1 | 2/2002 | Adams et al. |
| 6,478,210 B2 | 11/2002 | Adams et al. |
| 6,585,144 B2 | 7/2003 | Adams et al. |
| 6,601,749 B2 | 8/2003 | Sullivan et al. |
| 6,629,630 B2 | 10/2003 | Adams |
| 6,632,227 B2 | 10/2003 | Adams |
| 6,695,198 B2 | 2/2004 | Adams et al. |
| 6,820,791 B2 | 11/2004 | Adams |
| 6,827,246 B2 | 12/2004 | Sullivan et al. |
| 6,840,423 B2 | 1/2005 | Adams et al. |
| 6,866,178 B2 | 3/2005 | Adams et al. |
| 6,874,669 B2 | 4/2005 | Adams et al. |
| 6,945,444 B2 | 9/2005 | Gresham et al. |
| 6,959,851 B2 | 11/2005 | Heinrich |
| 7,083,630 B2 | 8/2006 | DeVries et al. |
| 7,090,684 B2 | 8/2006 | McGuckin, Jr. et al. |
| 7,168,604 B2 | 1/2007 | Milliman et al. |
| 7,234,624 B2 | 6/2007 | Gresham et al. |
| 7,303,106 B2 | 12/2007 | Milliman et al. |
| 7,810,690 B2 | 10/2010 | Bilotti et al. |
| 8,181,840 B2 | 5/2012 | Milliman |
| 9,463,023 B2 * | 10/2016 | Racenet ............... A61B 17/115 |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2003/0019905 A1 | 1/2003 | Adams et al. |
| 2003/0127491 A1 | 7/2003 | Adams et al. |
| 2003/0132267 A1 | 7/2003 | Adams et al. |
| 2003/0192937 A1 | 10/2003 | Sullivan et al. |
| 2004/0134964 A1 | 7/2004 | Adams et al. |
| 2004/0193184 A1 | 9/2004 | Laufer et al. |
| 2004/0232198 A1 | 11/2004 | Adams et al. |
| 2005/0145675 A1 | 7/2005 | Hartwick et al. |
| 2005/0205640 A1 | 9/2005 | Milliman |
| 2006/0151568 A1 | 7/2006 | Weller et al. |
| 2006/0155308 A1 | 7/2006 | Griego |
| 2006/0191975 A1 | 8/2006 | Adams et al. |
| 2006/0241692 A1 | 10/2006 | McGuckin et al. |
| 2007/0023475 A1 | 2/2007 | Csiky |
| 2007/0233161 A1 | 10/2007 | Weller et al. |
| 2008/0078808 A1 | 4/2008 | Hess et al. |

* cited by examiner

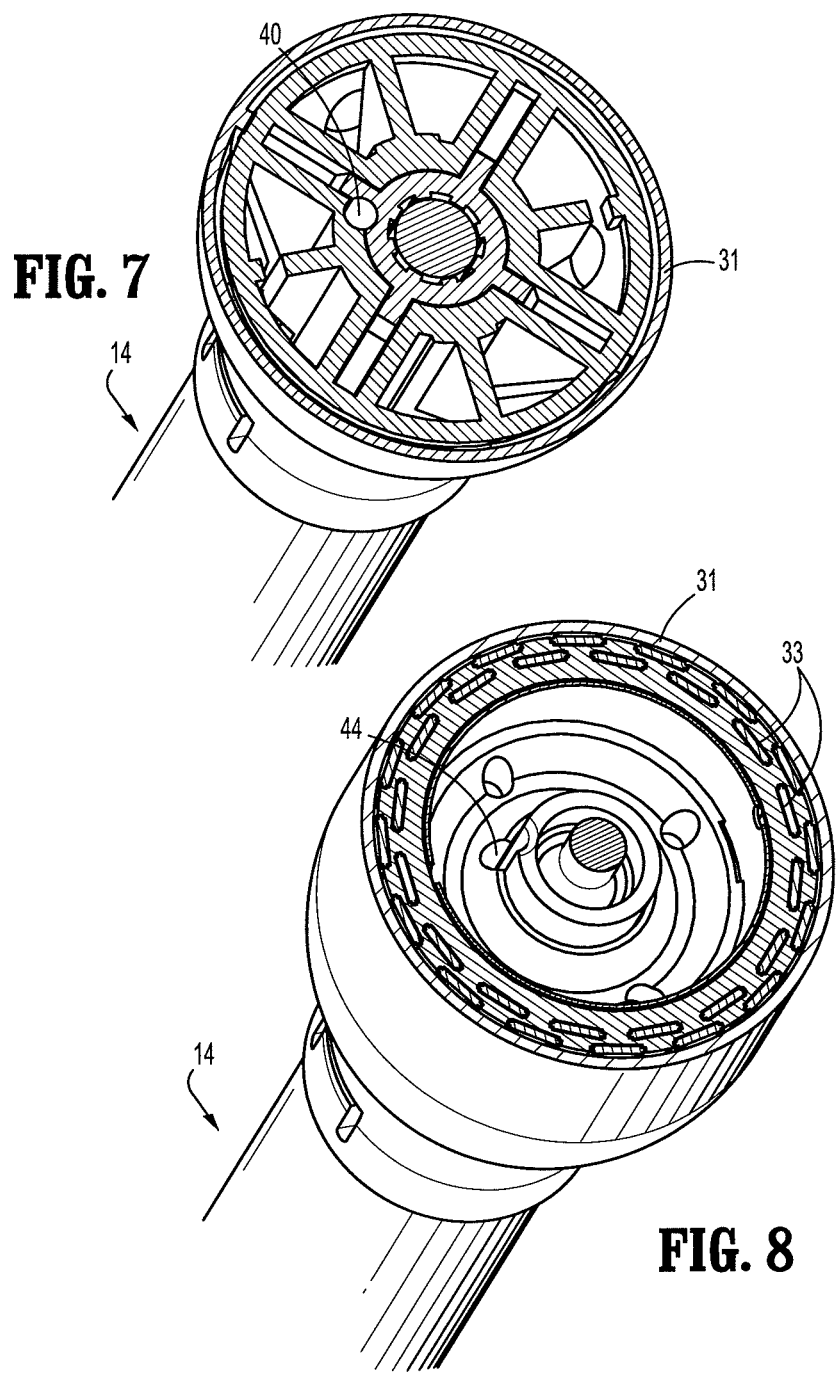

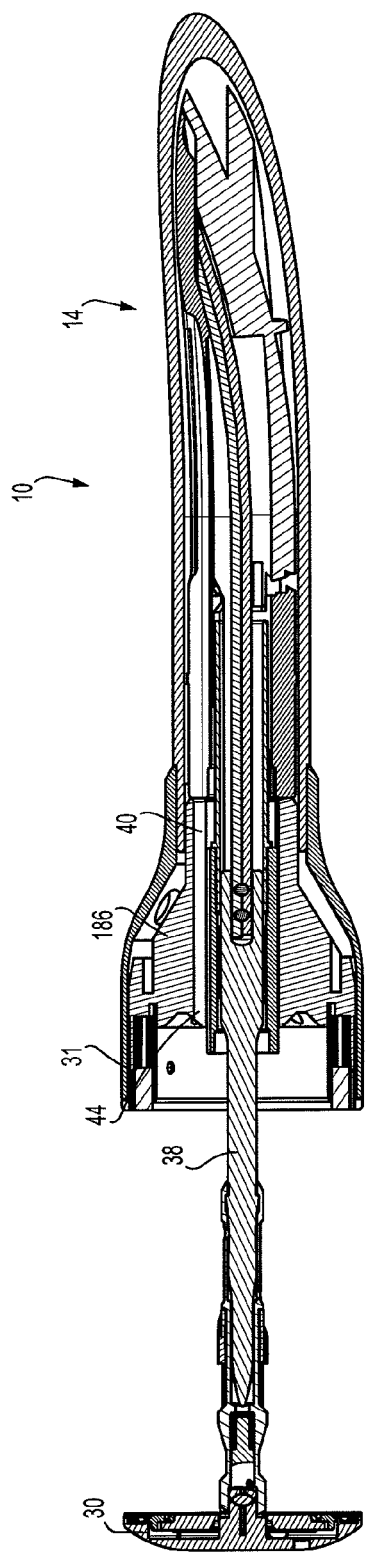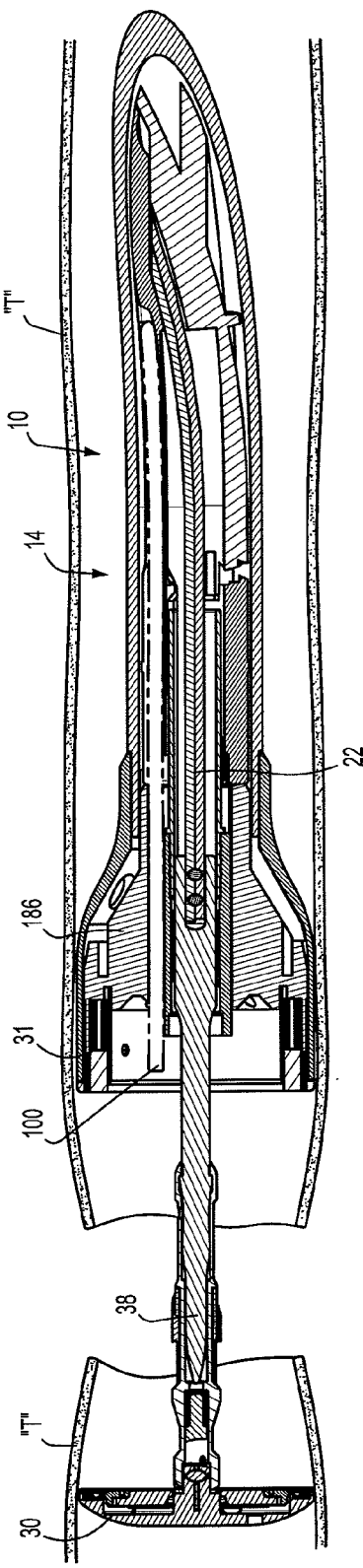
FIG. 10
FIG. 11

SURGICAL INSTRUMENT WITH ELONGATED CHANNEL

CROSS-REFERENCE TO RELATED APPLICATIONS

This application is a continuation of U.S. patent application Ser. No. 14/183,573 filed Feb. 19, 2014, which is a divisional of U.S. patent application Ser. No. 12/486,826 filed Jun. 18, 2009, now U.S. Pat. No. 8,678,264, which claims benefit of U.S. Provisional Application No. 61/078,460 filed Jul. 7, 2008, and the disclosures of each of the above-identified applications are hereby incorporated by reference in their entirety.

BACKGROUND

Technical Field

The present disclosure relates generally to a surgical stapling device for applying surgical staples to body tissue. More particularly, the present disclosure relates to a surgical stapling device suitable for performing circular anastomosis and/or treatment to internal walls of hollow tissue organs.

Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,945,444, 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil. An annular knife is concurrently advanced to core tissue within the hollow organ to free a tubular passage within the organ.

Besides anastomosis of hollow organs, surgical stapling devices for performing circular anastomosis have been used to treat internal hemorrhoids in the rectum. Typically, during use of a circular stapling device for hemorrhoid treatment, the anvil head and the staple holding component of the surgical stapling device are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling device is fired to remove the hemorrhoidal tissue and staple the cut tissue.

In certain situations, it is desirable to use an endoscope and/or an illumination device while performing an anastomosis. In such circumstances, surgeons typically create an additional opening in the patient to allow passage of such instruments.

Accordingly, it would be advantageous to provide a surgical stapling instrument which would enable illumination or visualization without requiring an additional opening in the patient. It would also be advantageous if such instrument could further enable introduction of fluids or other instrumentation without requiring removal of the instrument or requiring additional clamping and equipment.

SUMMARY

The present disclosure relates to a surgical stapling instrument including a handle assembly, an elongated body portion, a head portion and an elongated channel. The elongated body portion extends distally from the handle assembly. The head portion is disposed adjacent a distal end of the elongated body portion and includes an anvil assembly and a shell assembly. The elongated channel includes a proximal opening and a distal opening. The proximal opening is disposed distally of a proximalmost end of the handle assembly and proximally of the shell assembly. The distal opening is disposed on the shell assembly. In an exemplary embodiment, the proximal opening is disposed proximally of a midpoint of the elongated body portion and distally of the handle assembly.

The present disclosure also relates in another aspect to a method of performing a surgical procedure. The method includes the step of providing a surgical instrument including a handle assembly, an elongated body portion, a head portion and an elongated channel. The elongated body portion extends distally from the handle assembly. The head portion is disposed adjacent a distal end of the elongated body portion. The elongated channel extends through a majority of a length of the elongated body portion. A proximal opening of the elongated channel is disposed distally of a proximalmost end of the handle assembly. The method also includes the steps of positioning the surgical instrument adjacent a surgical site, and inserting a second surgical instrument through the proximal opening of the elongated channel and out of a distal opening of the elongated channel, such that at least a portion of the second surgical instrument is adjacent the surgical site.

DESCRIPTION OF THE DRAWINGS

Various embodiment of the presently disclosed surgical stapling device are disclosed herein with reference to the drawings, wherein:

FIG. 7 is a perspective, partial cut-away view of the surgical instrument of the present disclosure showing a transverse cross-section along line 7-7 of FIG. 3;

FIG. 8 is a perspective, partial cut-away view of the surgical instrument of the present disclosure showing a transverse cross-section along line 8-8 of FIG. 3;

FIG. 10 is a longitudinal cross-sectional view of the surgical instrument of the present disclosure taken along line 10-10 of FIG. 9; and FIG. 11 is a view similar to FIG. 10 showing the instrument inserted into tissue and with a second surgical instrument inserted therethrough.

DETAILED DESCRIPTION OF EMBODIMENTS

Figure 1:
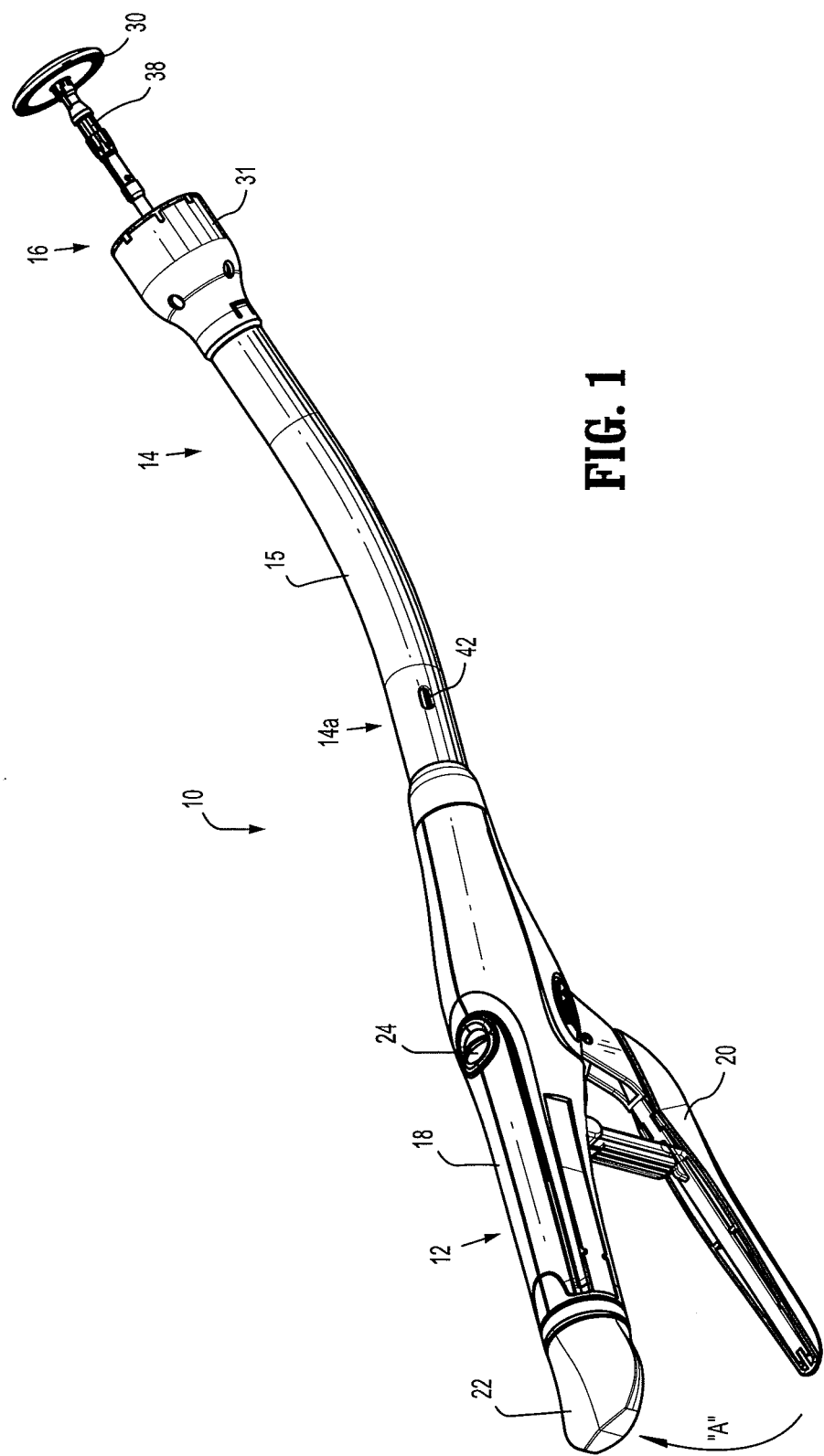
FIG. 1 is a perspective view of the presently disclosed surgical stapling instrument in an unapproximated position.

Embodiments of the presently disclosed surgical stapling instrument will now be described in detail with reference to the drawings in which like reference numerals designate identical or corresponding elements in each of the several views.

Throughout this description, the term "proximal" will refer to the portion of the instrument closer to the operator and the term "distal" will refer to the portion of the instrument further from the operator.

With initial reference to FIG. 1, an embodiment of the presently disclosed surgical stapling device is shown generally as reference number 10. Briefly, surgical stapling device 10 includes a handle assembly 12, an elongated body portion 14 including a curved elongated outer tube 15, and a head portion 16. Alternately, in some surgical procedures, e.g., the treatment of hemorrhoids, it is desirable to have a substantially straight body portion. The length, shape and/or the diameter of body portion 14 and head portion 16 may also be varied to suit a particular surgical procedure.

In the illustrated embodiments, handle assembly 12 includes a stationary handle 18, a firing trigger 20, a rotatable approximation knob 22 and an indicator 24. Head portion 16 includes an anvil assembly 30 and a shell assembly 31. Anvil assembly 30 is movable in relation to shell assembly 31 between spaced (unapproximated) and approximated positions. Anvil assembly includes an anvil shaft 34 mounted (preferably removably mounted) to the anvil retainer 38. An elongated channel 40 is disposed through a majority of the length of elongated body portion 14.

In operation, rotation of approximation knob 22 causes movement of anvil assembly 30 in relation to shell assembly 31 between spaced and approximated positions, as approximation knob 22 is mechanically engaged with anvil retainer 38 via bands 22, which is connected to anvil assembly 30. It is envisioned that rotation of approximation knob 22 in a first direction (e.g., clockwise) causes proximal movement of anvil assembly 30 to an approximated position and rotation of approximation knob 22 in a second opposite direction (e.g., counter-clockwise) causes distal movement of anvil assembly 30 to an unapproximated position.

Actuation of firing trigger 20 (i.e., pivoting in the direction of arrow "A" in FIG. 1), causes staples to be ejected from shell assembly 31 towards anvil assembly 30. That is, firing trigger 20 is disposed in mechanical cooperation with a pusher 186 (see FIGS. 10 and 11) such that actuation of firing trigger 20 causes advancement of pusher 186 into contact with the staples, which forces the staples out of staple pockets 33 into staple deforming pockets of anvil assembly 30.

Further details of other features of surgical stapling device 10, such as the approximation assembly and firing assembly are disclosed in commonly-owned U.S. Pat. Nos. 7,303,106, 7,234,624 and 7,168,604, the entire contents of which are incorporated by reference herein.

Figure 2:
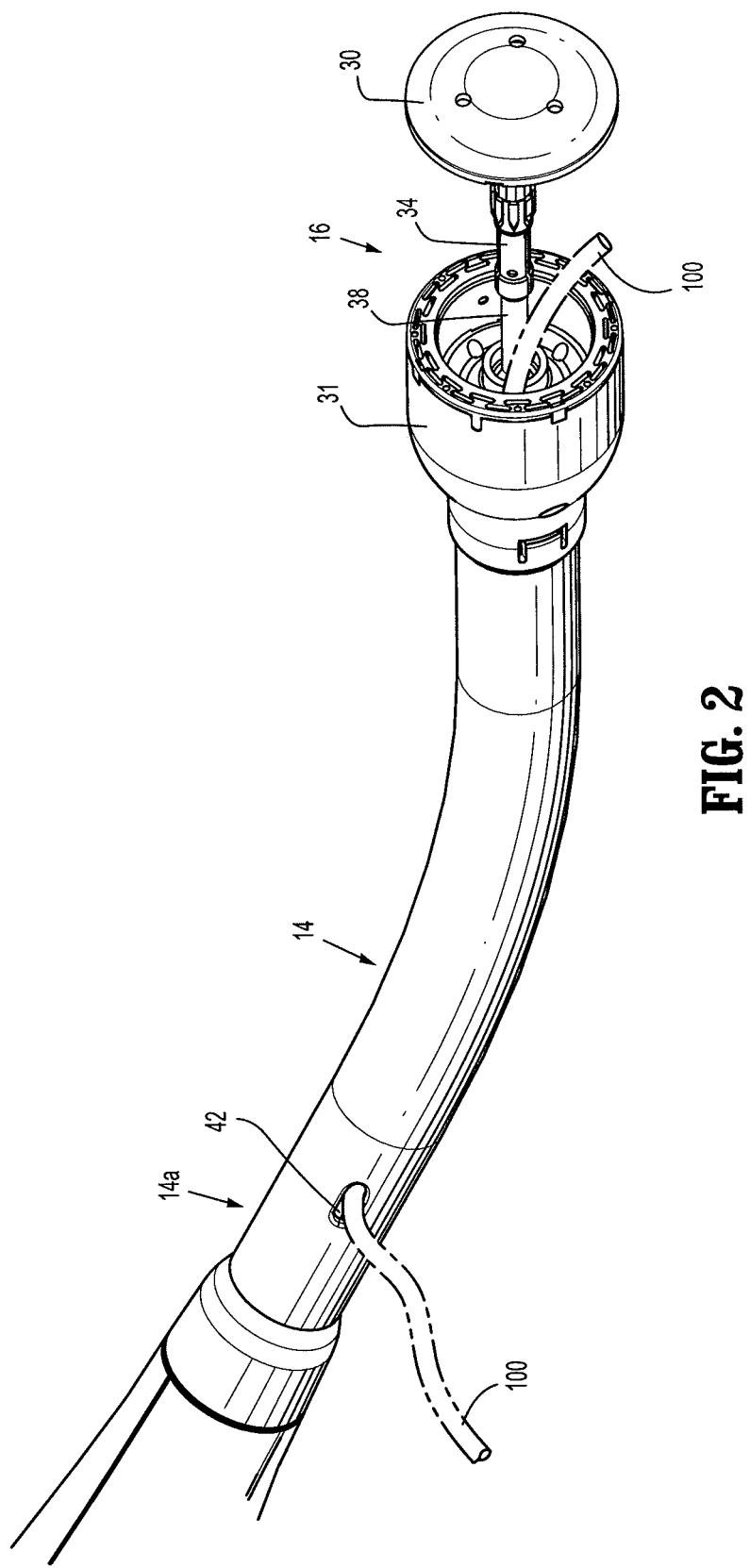
FIG. 2 is a perspective view of a portion of the surgical stapling instrument of FIG. 1 showing a second surgical instrument inserted therethrough.
Figure 3:
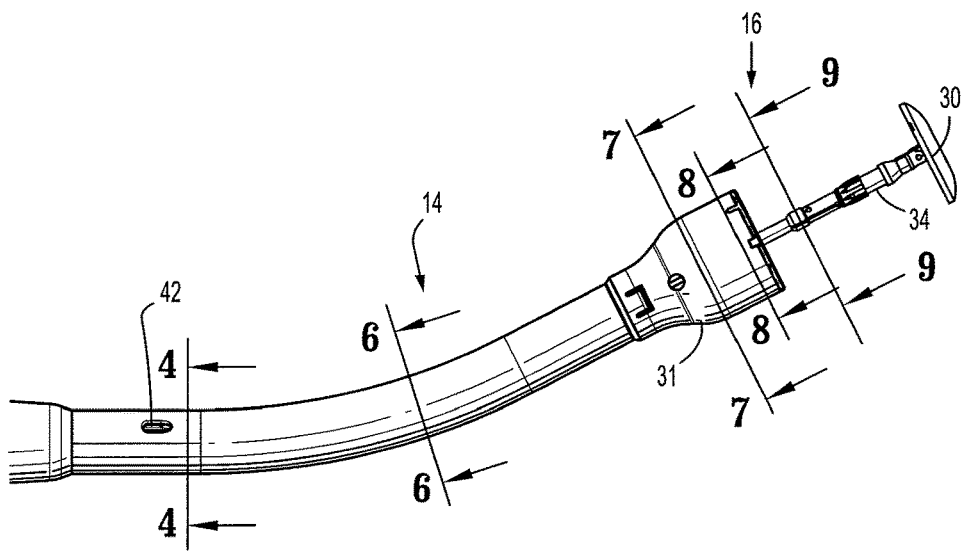
FIG. 3 is a side view of a portion of the surgical stapling instrument of FIG. 1.
Figure 4:
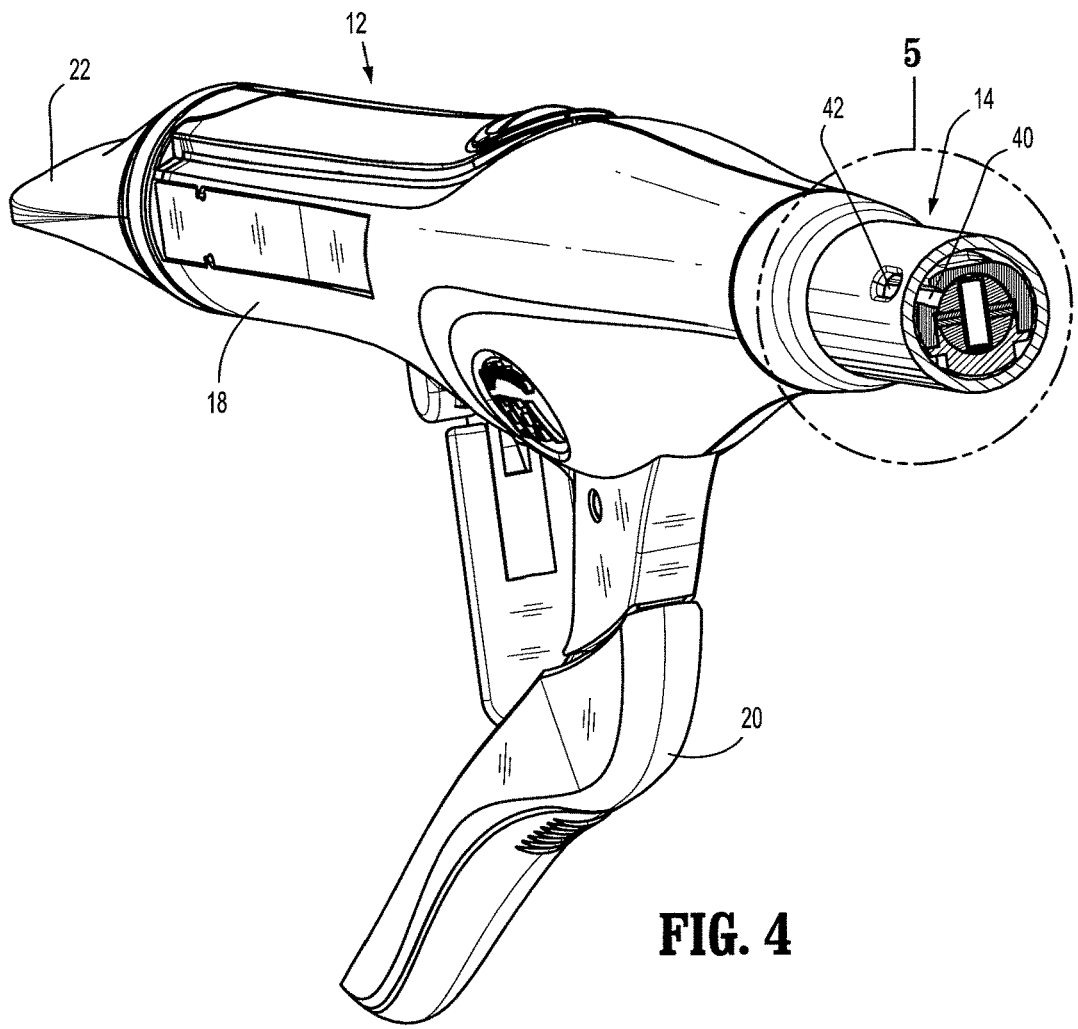
FIG. 4 is a perspective, partial cut-away view of the surgical instrument of the present disclosure showing a transverse cross-section along line 4-4 of FIG. 3
Figure 5:
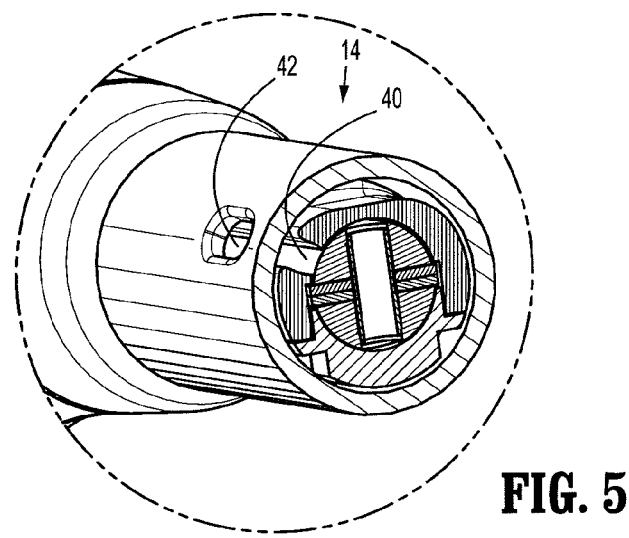
FIG. 5 is an enlarged view of the surgical instrument of the present disclosure in the indicated area of detail shown in FIG. 4.
Figure 6:
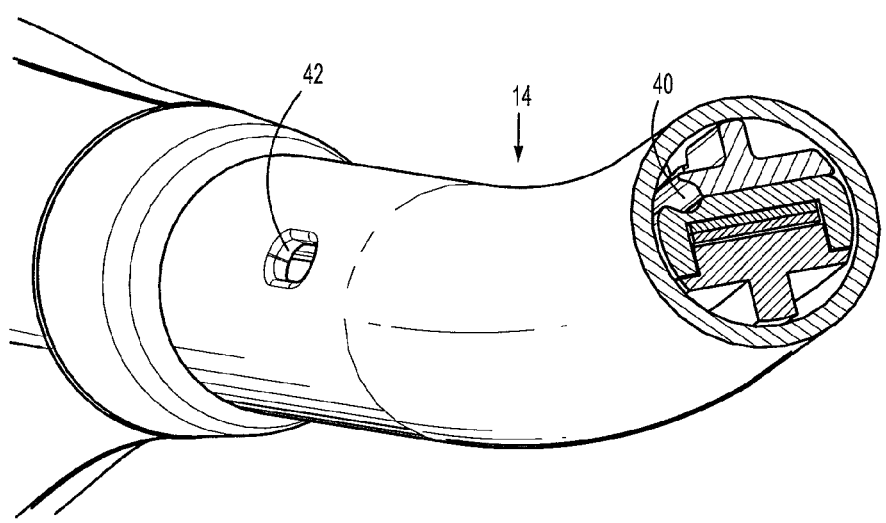
FIG. 6 is a perspective, partial cut-away view of the surgical instrument of the present disclosure showing a transverse cross-section along line 6-6 of FIG. 3.

In the illustrated embodiments, elongated channel 40 includes a proximal opening 42 (see FIGS. 2-6) and a distal opening 44 (see FIGS. 8-10) and is configured to allow another instrument 100 (FIG. 2) to pass therethrough. As shown, proximal opening 42 is disposed distally of a proximalmost end of the handle assembly 12 and proximal of the shell assembly 31, and preferably distally of the handle assembly 12 at a proximal portion 14a of elongated body portion 14 (i.e. proximally of the midpoint of the elongated body portion). Distal opening 44 is disposed on a distal-facing surface of shell assembly 31. The positioning of proximal opening 42 allows a second surgical instrument 100 to be inserted through surgical stapling device 10 and into tissue "T" (e.g., adjacent the surgical site; see FIG. 11). Since proximal opening 42 is disposed distally of handle assembly 12, elongated channel 40 does not interfere with any of the internal working components of handle assembly 12. Additionally, since proximal opening 42 is disposed at proximal portion 14a of elongated body portion 14, insertion of second surgical instrument 100 is facilitated when a distal portion of surgical stapling device 10 (e.g., head portion 16) is adjacent a target tissue site.

Figure 9:
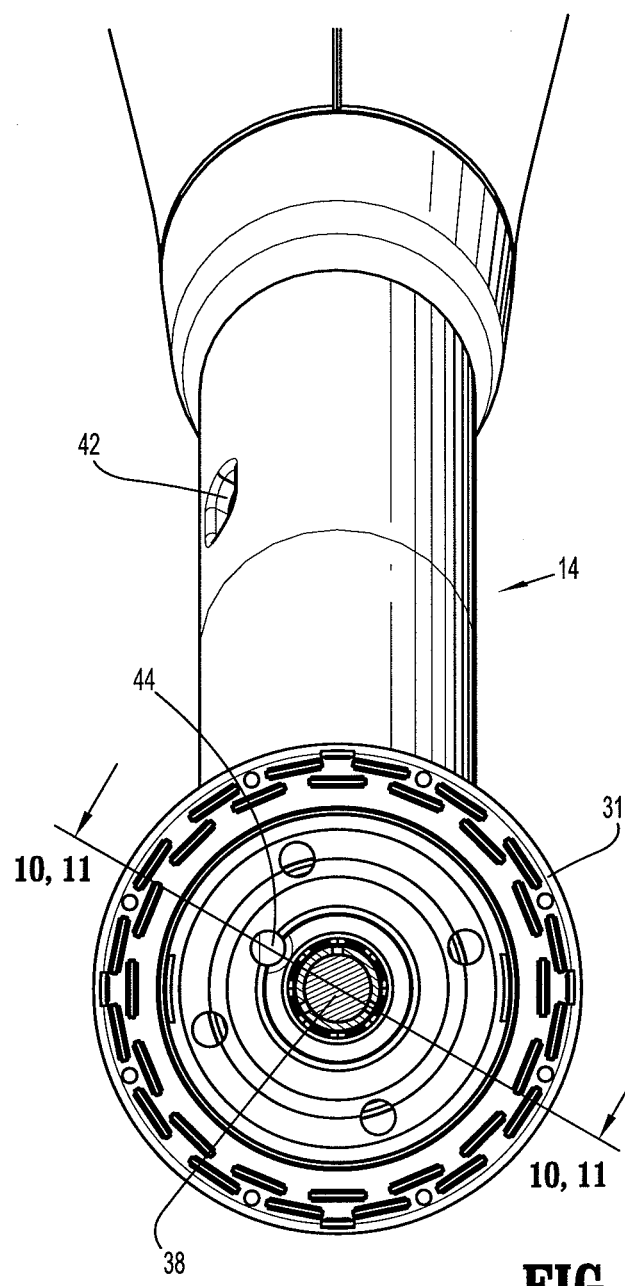
FIG. 9 is a perspective, partial cut-away view of the surgical instrument of the present disclosure showing a transverse cross-section along line 9-9 of FIG. 3.

With reference to FIGS. 7-9, distal opening 44 is displaced from an axial center (indicated by center of anvil retainer 38) of shell assembly 31 (see FIG. 9). This location of distal opening 44 helps ensure that elongated channel 40 does not interfere with the moving parts (e.g., pusher 186) of shell assembly 31. In one embodiment by way of example, the distal opening 44 is displaced in the range of about 0.20 inches to about 0.30 inches from the axial center of shell assembly 31. Other spacings are also contemplated.

Additionally, in FIGS. 1-3 and 6 elongated body portion 14 is illustrated having a longitudinally curved portion, which may be helpful for certain types of surgical procedures. While not explicitly illustrated, it is envisioned that elongated body portion 14 can include a bent portion or be substantially straight along its length. In embodiments where elongated body portion 14 is curved, elongated channel 40 may also include a curved portion, e.g., to accommodate a curved and/or flexible instrument.

In alternate embodiments where elongated body portion 14 is curved (or bent), elongated channel 40 may be substantially straight along its entire length. In these embodiments, it is envisioned that proximal opening 42 of elongated channel 40 is disposed proximally adjacent the bend or an apex of the curve, such that a straight, non-flexible surgical instrument can be inserted through elongated body portion 14 and out distal opening 44 to be adjacent the surgical site.

Elongated channel 40 is configured to allow a device to be passed therethrough, and in a preferred embodiment, is configured to allow an endoscope or an illumination device to pass therethrough. In such embodiments, a user is able to insert the endoscope and/or illumination device (e.g., to inspect staple lines) without having to remove surgical stapling device 10 from the patient. Additionally, fluids (e.g., saline or a leak-testing dye to verify staple line integrity) can be passed through elongated channel 40 to the surgical site.

Also, flexible instruments can be inserted. In one embodiment, the diameter of elongated channel 40 is between about 0.115 inches and about 0.135 inches. Other dimensions are also contemplated.

The present disclosure also relates to a method of performing a surgical procedure. The method includes the steps of providing surgical instrument 10 (such as that described hereinabove), positioning surgical stapling device 10 adjacent a surgical site, and inserting second surgical instrument 100 through proximal opening 42 of elongated channel 40 and out of distal opening 44 of elongated channel 40, such that at least a portion of second surgical instrument 100 is adjacent the surgical site.

It will be understood that various modifications may be made to the embodiments disclosed herein. Therefore, the above description should not be construed as limiting, but merely as exemplifications of disclosed embodiments. For instance, while a specific type of a surgical stapling device is shown, other types of surgical devices are within the scope of the present disclosure. Those skilled in the art will envision other modifications within the scope and spirit of the claims appended hereto.

What is claimed:

1. A surgical stapling instrument, comprising:
   a handle assembly;
   an elongate body portion extending distally from the handle assembly;
   a head portion disposed adjacent a distal end of the elongate body portion, the head portion including an anvil assembly and a shell assembly, the anvil assembly movable relative to the shell assembly; and
   an elongate channel configured to receive a surgical object therethrough, the elongate channel including a proximal opening and a distal opening, the elongate channel extending at least a length of the elongate body portion, the proximal opening disposed proximal of the shell assembly and proximal of a longitudinal midpoint of the elongate body portion, the distal opening disposed on the shell assembly.

2. The surgical stapling instrument of claim 1, wherein the proximal opening of the elongate channel is distal of a proximal-most end of the handle assembly.

3. The surgical stapling instrument of claim 1, wherein the proximal opening of the elongate channel is adjacent a proximal portion of the elongate body portion.

4. The surgical stapling instrument of claim 1, wherein the distal opening is displaced from an axial center of the shell assembly.

5. The surgical stapling instrument of claim 4, wherein the distal opening of the elongate channel is displaced in a range from about 0.20 inches to about 0.30 inches from the axial center of the shell assembly.

6. The surgical stapling instrument of claim 1, wherein the distal opening of the elongate channel is disposed at a distal surface of the shell assembly.

7. The surgical stapling instrument of claim 1, wherein the proximal opening of the elongate channel is distal of the handle assembly.

8. The surgical stapling instrument of claim 1, wherein the elongate body portion has a uniform diameter.

9. The surgical stapling instrument of claim 1, wherein a diameter of the elongate channel is in a range from about 0.115 inches to about 0.135 inches.

10. The surgical stapling instrument of claim 1, wherein the elongate body portion includes a curved portion.

11. The surgical stapling instrument of claim 1, wherein the proximal and distal openings of the elongate channel are in fluid communication.

12. The surgical stapling instrument of claim 1, wherein the proximal opening of the elongate channel is defined in a side wall of the elongate body portion.

13. A surgical stapling instrument, comprising:
    a handle assembly;
    an elongate body portion extending distally from the handle assembly, distal-most and proximal-most ends of the elongate body portion having the same diameter;
    a head portion disposed adjacent a distal end of the elongate body portion and including a shell assembly and an anvil assembly movable relative to the shell assembly; and
    an elongate channel including a proximal opening and a distal opening, the proximal opening disposed in a side wall of the elongate body portion, wherein the elongate channel extends at least a length of the elongate body portion such that the elongate channel provides a surgical object inserted through the elongate channel access to a surgical site.

14. The surgical stapling instrument of claim 13, wherein the elongate body portion includes a curved portion.

15. The surgical stapling instrument of claim 13, wherein at least a portion of the elongate channel is completely surrounded by the side wall of the elongate body portion.

* * * * *